US007988909B1

(12) United States Patent
Ruan

(10) Patent No.: US 7,988,909 B1
(45) Date of Patent: Aug. 2, 2011

(54) METHOD AND APPARATUS FOR CONDITIONING ROOM AIR

(76) Inventor: Ying Gang Ruan, Overland Park, KS (US)

( * ) Notice: Subject to any disclaimer, the term of this patent is extended or adjusted under 35 U.S.C. 154(b) by 0 days.

(21) Appl. No.: 12/784,252

(22) Filed: May 20, 2010

(51) Int. Cl.
*A61L 9/00* (2006.01)
*A61L 9/14* (2006.01)
*A62L 2/18* (2006.01)

(52) U.S. Cl. .................. 422/4; 422/5; 422/28; 422/120; 423/210; 96/329; 96/351; 95/223; 95/226; 95/230; 55/DIG. 27

(58) Field of Classification Search .................. 423/210; 422/4, 5, 28, 120; 96/329, 351; 95/223, 95/226, 230; 55/DIG. 27
See application file for complete search history.

(56) References Cited

U.S. PATENT DOCUMENTS

| 251,407 | A | | 12/1881 | Bruns |
| 1,374,689 | A | * | 4/1921 | Torrey ............................ 95/214 |
| 5,078,759 | A | | 1/1992 | Kira |
| 5,143,527 | A | | 9/1992 | Tian-Song |
| 5,221,520 | A | * | 6/1993 | Cornwell ....................... 422/122 |
| 5,225,158 | A | * | 7/1993 | Tayebi et al. ...................... 422/4 |
| 5,409,834 | A | * | 4/1995 | Birdwell .................... 435/294.1 |
| 5,908,491 | A | | 6/1999 | Hobbs |
| 7,163,571 | B2 | | 1/2007 | Ruan |
| 7,252,703 | B2 | * | 8/2007 | MacKnight ..................... 95/218 |
| 2008/0271603 | A1 | * | 11/2008 | Triplett et al. .................. 95/150 |

FOREIGN PATENT DOCUMENTS

JP 58-008360 A * 1/1978

* cited by examiner

*Primary Examiner* — Timothy Vanoy
(74) *Attorney, Agent, or Firm* — Hovey Williams LLP

(57) ABSTRACT

A method and apparatus for conditioning the air within an interior area, includes a fan, a first module receiving air from the fan and preferably a first liquid, and a second module receiving air from the first module and preferably including a second liquid. The modules are preferably stacked, whereby air enters the fan module on the bottom and is delivered to the environment from the second module at the top. The air flows from the fan along a pathway which prevents liquid from escaping from the modules other than as vapor entrained in the air. The first liquid is preferably an aqueous alkaline solution, and the second liquid preferably includes a disinfectant and/or a buffer to neutralize the alkaline before air is delivered to the environment. The modules may have an inner wall and an outer wall presenting a dead-air space therebetween.

35 Claims, 5 Drawing Sheets

METHOD AND APPARATUS FOR CONDITIONING ROOM AIR

BACKGROUND OF THE INVENTION

1. Field of the Invention

The present invention is concerned with an apparatus and method for delivering ambient air through at least one, and preferably sequentially through a plurality of chambers wherein the ambient air is passed through a chamber containing a liquid to cool the air and remove contaminants. Preferably, the present invention includes a fan chamber and a downstream chamber wherein the air is diffused and passed through a liquid which contains a decontaminating chemical prior to delivery to a room within a building or other contained space.

2. Description of the Prior Art

Many people suffer from allergies or breathing problems as a result of contaminants in the air or dry air within a heated space. The presence of pollen, dust and airborne pollution cause discomfort, and in addition, airborne viruses and bacteria may pose a health hazard. While vaporizers using either cooled or heated air serve to add humidity to a space, they do little to remove contaminants or inhibit the inhalation of airborne disease.

A variety of different air filtration or aeration devices have been developed, including those set forth in U.S. Pat. Nos. 251,407, 5,078,759, 5,143,527 and 5,908,491, but these devices do not address the need for a system readily usable in the home or office environment, which can be maintained by the user, and both humidifies and disinfects the air. An improved device for conditioning room air is shown in my U.S. Pat. No. 7,163,571, the entire disclosure of which is incorporated herein by reference, but further improvements are possible.

SUMMARY OF THE INVENTION

These and other needs have largely been met by my method and apparatus for conditioning room air. That is to say, my invention not only circulates air through water to purify and humidify the air, but inhibits spillage, collects contaminants, and disinfects the air passing through the conditioner hereof.

Broadly speaking, my invention includes a device which passes ambient air through at least one, and preferably a plurality of liquid-containing chambers in order to capture contaminants in the chambers, cool the air, and humidify the air delivered to the space. Preferably, at least one of the chambers includes an aqueous alkaline (i.e., base) solution. The air is delivered to and from the chamber through a pathway which reduces the escape of liquid by a baffle arrangement, so that any liquid other than in vapor form is returned or captured in the device. Preferably, this baffle system causes the path of the air to move in a path which has three axes of movement.

Additionally, the present invention may include a second liquid-containing chamber located downstream from the first chamber, whereby air which passes through the first liquid is thereafter passed through a second liquid. The second liquid may be water, which helps to dilute, remove, and/or neutralize any residual base in the air carried from the first chamber, and may include a disinfectant, such as, for example, an aqueous sodium hypchlorite solution, to further treat and disinfect the air passing therethrough. In preferred embodiments, the first chamber is part of a first module mounted atop and interfitting with a fan module, and the second chamber is part of a second module interfitting with and mounted atop the first module. This modular construction aids in servicing and transporting the device. Also in preferred embodiments, the air is introduced into the liquid in the second chamber by a floating sparging device, whereby as the level of the liquid in the second chamber rises and falls, the position of the sparging device relative to the water level remains substantially constant. Most preferably, the housings of each module include a dead-air space along each side wall to reduce the sound emitted by the apparatus, and a pair of sound isolation panels in the air intake to reduce emitted sound.

One method of the present invention includes the steps of providing a fan and at least a first liquid-filled chamber having an aqueous base solution, forcing air from the fan through a diffuser within the base solution, and passing the air around a baffle prior to delivery to the atmosphere. More preferably, the method includes the further steps of passing the air from the base solution through a second liquid prior to delivery to the atmosphere, and most preferably the second liquid including a disinfectant or neutralizing agent.

The invention further includes a method for treating a stream of air containing contaminants. The method includes the steps of contacting an initial stream of air to be treated with a first liquid comprising an aqueous alkaline solution to yield a first treated air stream. The first treated air stream is contacted with a second liquid different from the first liquid and comprising water to yield a second treated air stream. Advantageously, the second treated air stream comprises substantially less contaminants than the initial stream of air to be treated.

These and other advantages of the present invention will be readily apparent to those skilled in the art with reference to the drawings and description which follow.

DESCRIPTION OF THE PREFERRED EMBODIMENT

Figure 1:
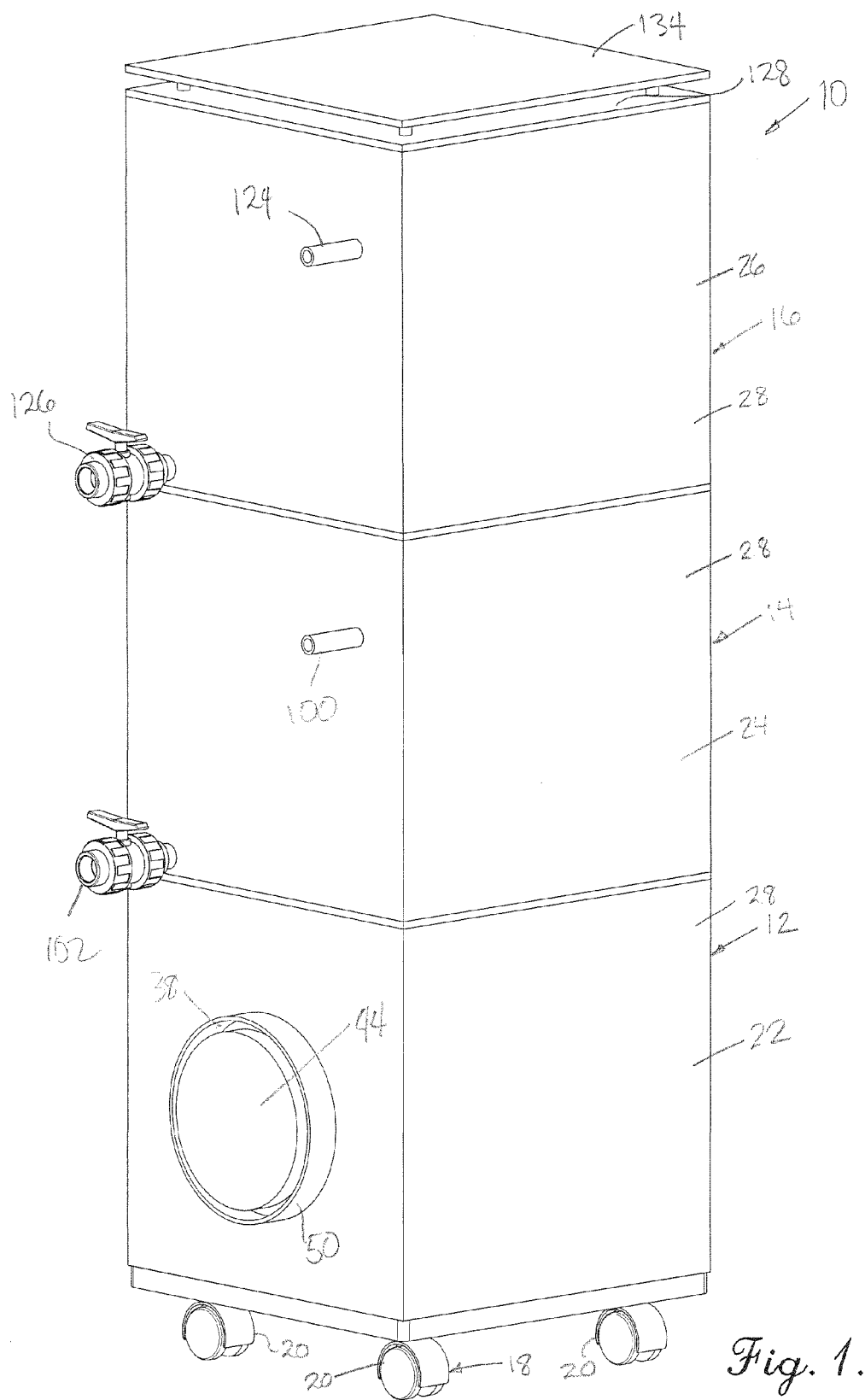
FIG. 1 is a left rear perspective view of the device of the present invention, showing a fan module having an air intake positioned beneath a first module which has an inlet for filling a first chamber and a discharge outlet for draining the first chamber, with a second module having a second chamber mounted atop the first chamber also having an inlet for filling and a discharge outlet for draining the second chamber, and a diffuser for the conditioned air positioned atop the second module.

Referring now to the drawing, an apparatus 10 for conditioning ambient air is typically placed within a room of a building and broadly includes a fan module 12 which receives ambient air from a room in which the apparatus 10 is placed, a first module 14 for receiving forced air from the fan module 12, and a second module 16 which receives air conditioned by the first module 14, performs additional conditioning, and then passes the air back into the ambient environment of the room. The fan module 12, first module 14, and second module 16 are most preferably arranged in vertically stacked relationship as shown in FIG. 1, and the fan module 12, when lowermost, may have a wheeled carriage 18 which may include casters 20 capable of supporting the stacked modules and facilitating their collective movement. As shown in the drawings, each of the fan module 12, the first module 14 and the second module 16 have respective housings 22, 24 and 26 which are complementally configured for stacking. One way of accomplishing this stacking arrangement is by the use of flanges or feet extending downwardly into an open area defined within the upper edges of the sidewalls 28 of the respective housings 22, 24 and 26, such that the normally bottom walls of an upper module also serve as the upper wall of the module therebeneath. The sidewalls 28 most preferably include inner panel 30 and outer panel 32, defining therebetween a dead-air space 34 which may, if desired, include additional sound-deadening material such as fibrous glass. The dead-air space 34, which may be between about 0.125 and 2 inches and more preferably between about 0.25 and 1 inch between the inner panel 30 and outer panel 32, aids in reducing the sound developed within the housings 22, 24 and 26 resulting from operation of a fan 36 within the fan module 22 and the bubbling of air through the liquid contained in the first module 14 and second module 16. While it is also possible to provide these inner and outer panels 30 and 32 in the top and bottom walls of each of the respective housings 22, 24 and 26, because the modules are arranged in stacked relationship with the fan 36 and its motor largely isolated from the inlet and outlet of the apparatus by the various modules 12, 14 and 16 and the various baffles and sound suppression panels as well as the deflector as described and shown herein, the use of inner and outer walls for the top and bottom walls of each module is permissible, for example as shown in regard to the provision of inner and outer bottom walls in module 12 and its housing 22, but not necessary to provide for quiet operation.

Figure 3:
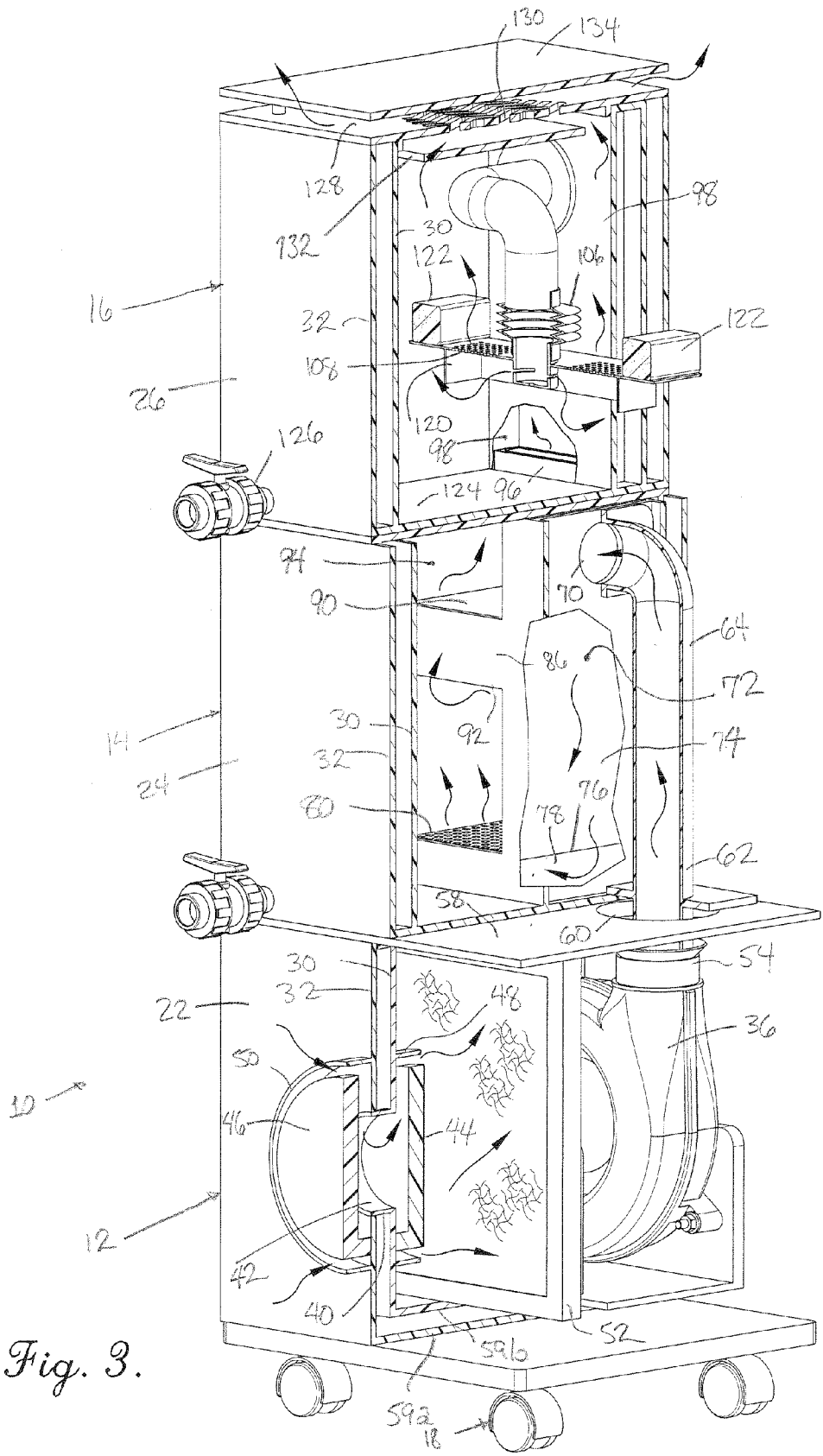
FIG. 3 left rear perspective view of a vertical cross-section with portions of the housings and baffles for the modules broken away to show the flowpath of the air entering the fan module and moving through the first and second modules.
Figure 4:
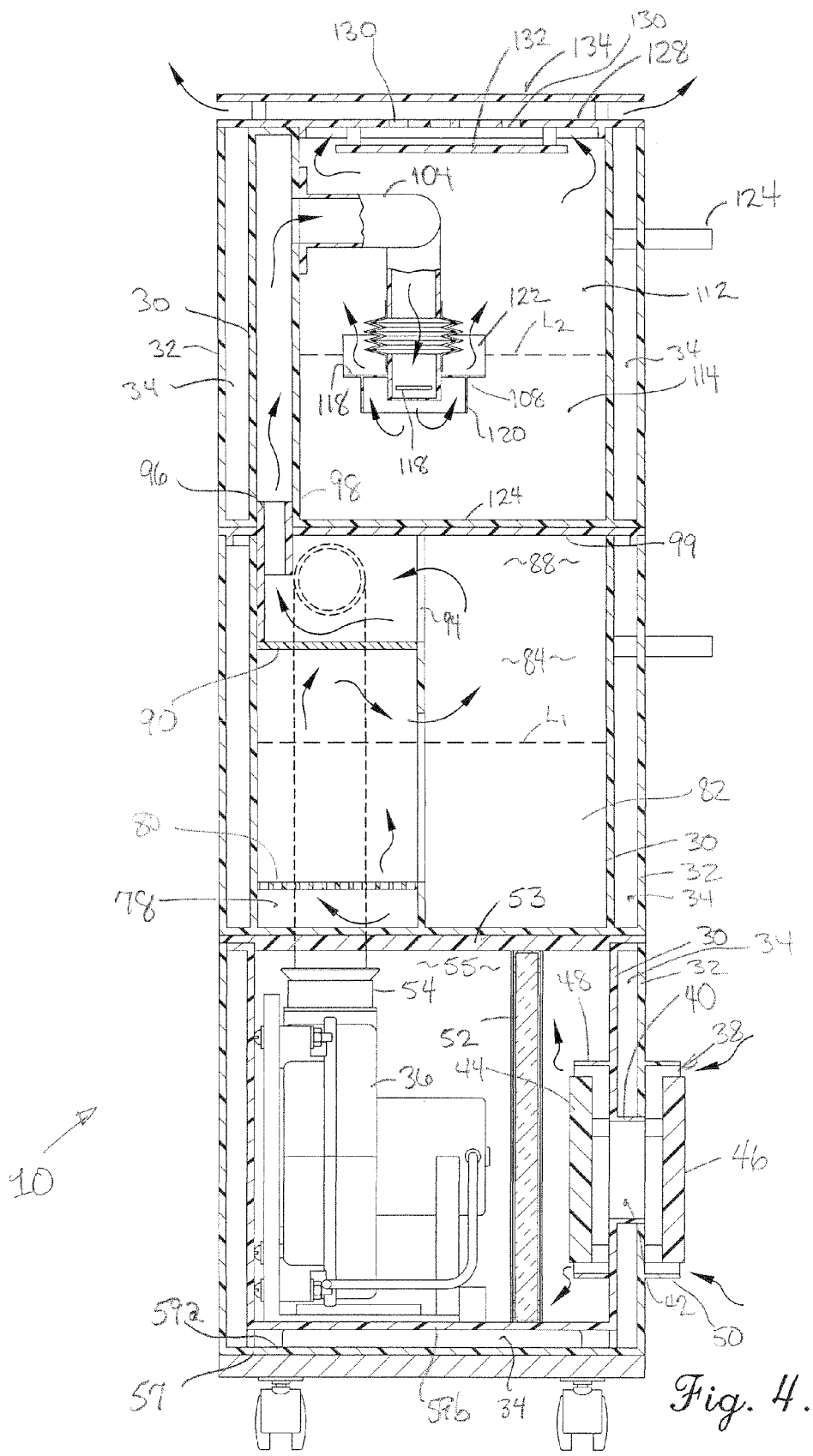
FIG. 4 is a vertical cross-sectional view taken from the right side of the present invention showing the flowpath of the ambient air entering the intake and into housing of the first module, then passing through the replaceable filter and into the fan before moving into the first chamber in the first module and into the second chamber of the second module and then upwardly through the top wall and around the deflector above the top wall.

In greater detail, the housing 22 of the fan module 12 has an inlet 38 which includes a connecting wall 40 and thus provides an opening 42 extending through each of the inner panel 30 and outer panel 32 for the admission of air into the fan module 12 of the apparatus 10. As best seen in FIGS. 3 and 4, inner panel 30 mounts an inner sound suppression panel 44 spaced interiorly of the opening 42 and the outer panel 32 mounts an outer sound suppression panel 46 spaced exteriorly of the opening 42. The sound suppression panels 44 and 46 are preferably sized larger than the opening 42 and placed in alignment with the opening 42. An inner rim 48 extends interiorly from the inner panel 30 circumferentially around and radially spaced from the inner sound suppression panel 44. Similarly, an outer rim 50 extends exteriorly from the outer panel 32 circumferentially around and radially spaced from the outer sound suppression panel 44. Ambient air from the room enters the fan module 12 by passing through the annular space between the outer sound suppression panel 46 and the outer rim 50, then through the opening 42, and then through the annular space between the inner sound suppression panel 44 and the inner rim 48.

Figure 2:
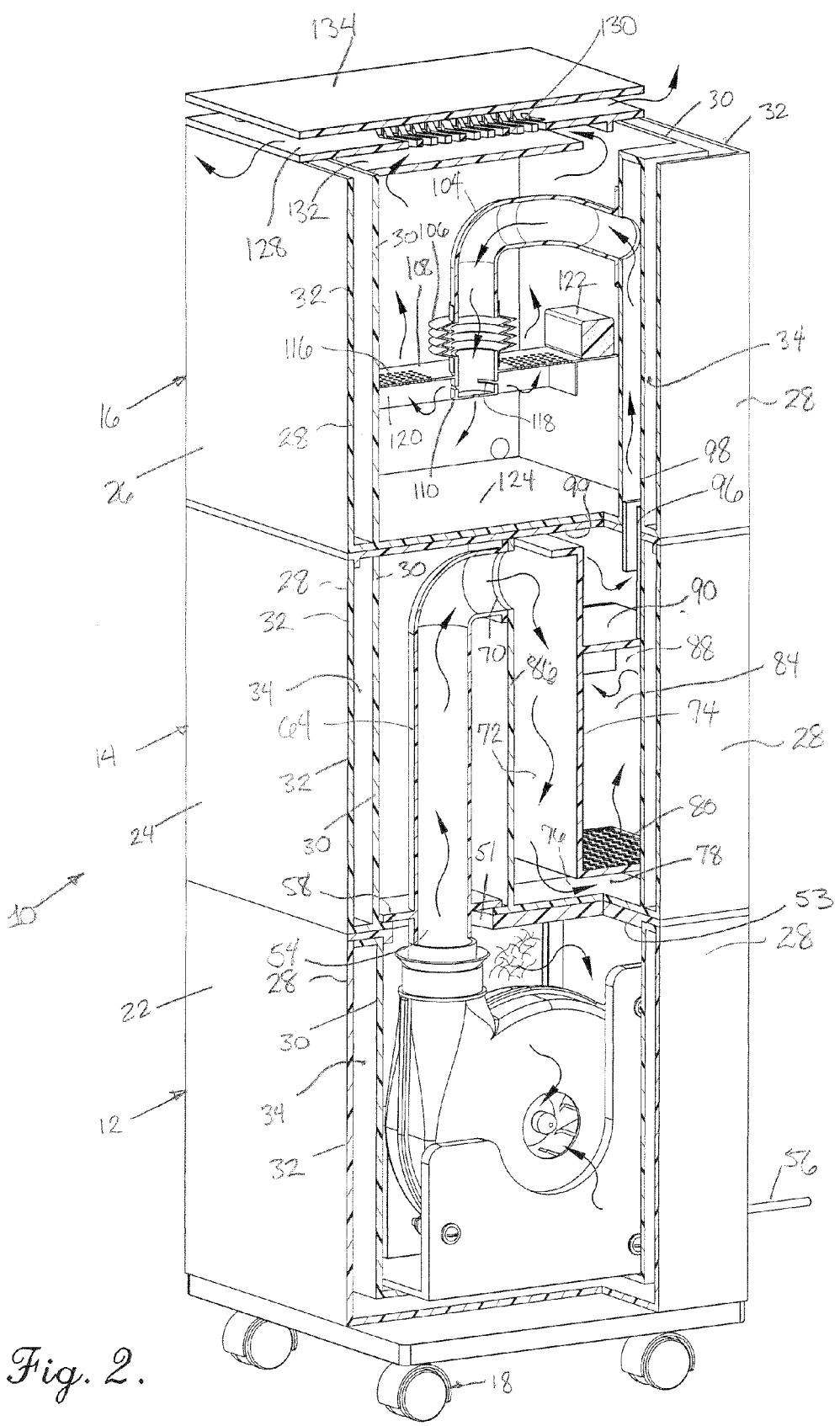
FIG. 2 is a left front perspective view of a vertical cross-section with portions of the housings and baffles for the modules broken away to show the fan and the flowpath of the air passing through the first and second modules and with portions of the top wall of the second module broken away to show the dead-air space in the side wall.

A filter element 52, having a filtering element of paper, fiber or other material known for usage in trapping airborne particles may be removably mounted by insertion through the open top of the fan housing 12, and positioned between the inlet 38 and the fan 36 so that air passing into the fan module 12 through opening 42 passes through the filter element 52 before entering fan 36 as shown in FIGS. 2 and 3. Fan 36 is mounted within the fan module 12 and is fluidically coupled to a duct 54 for delivering air driven by the fan 36 to the first module 14. The fan 36 is preferably electrically powered by a cord 56 which passes through the housing 22 and is connected to a receptacle in the room. The duct 54 extends through an opening 51 in a top wall 53 in the housing 22, the top wall 53 otherwise spanning the inner panel 30 and the outer panel 32 of the housing 22 to substantially enclose the chamber 55 therewithin. In the fan module 12, the housing further includes a bottom wall 57 having a lowermost bottom outer wall 59a and a bottom inner wall 59b spaced upwardly from the bottom outer wall 59a to provide a dead-air space 34 therebetween. The spacing between the bottom outer wall 59a and the bottom inner wall 59b may be about 0.125 to about 2 inches, and more preferably about 0.25 to about 1 inch, thereby helping to isolate the sound of fan 36 and its motor from the environment in the room in which the apparatus is placed.

The first module 14 is positioned atop the top wall 53 of the fan module 12 and receives air from the duct 54 which extends through a complementally sized opening in the top wall 53. As with fan module 12, the housing 24 of first module 14 has a surrounding side wall with an inner wall 30 and an outer wall 32 which substantially encloses the main chamber 84. The housing 24 has a bottom wall 58 which includes a port 60 in alignment with the opening 51 and duct 54 for receiving air from the fan 36 and delivering the air to a channel 62. The channel 62 includes a tunnel 64 which may be a rigid conduit or formed of walls which, in combination with the side walls, define the channel 62. The channel 62 extends upwardly from the port 60, and a window 70 is provided at the upper end of the sidewall 66. A return channel 72 is fluidically connected to the tunnel 64 so that air passing upwardly through the tunnel 64 is directed into the return channel 72. The return channel 72 has a panel 74 which includes an opening 76. The opening 76 is positioned below the liquid level in the first module 14, shown as dashed line $L_1$ in FIG. 5, but the configuration of the return channel 72 prevents liquid from flowing through the port 60 and back to the fan 36. As shown in FIG. 3, the air passing through the opening 76 is delivered into a diffusion chamber 78 located beneath a perforated diffuser panel 80. The diffuser panel 80 breaks up the air flow into small bubbles so that the air will then bubble up through the first liquid 82 in a first module main chamber 84 of the first module 14 thereby increasing the contact between the air and the first liquid 82. A connecting wall 86 connects with the sidewalls 28 of the housing 24 to contain the air and cause it to be diffused through the holes in the perforated diffuser panel 80. This breaks the air flowing into the diffusion chamber 78 into small bubbles in the first liquid 82 because the diffuser panel 80 is beneath the liquid level $L_1$. While portions of the connecting wall 86 are broken away for clarity in FIGS. 2 and 3, it is to be understood that the connecting wall 86 extends across the housing to also substantially enclose the return channel 72. The first module main chamber 84 holds the first liquid 82 within the first module 14, and the opening 76 permits the first liquid 82 to reside within the lower portion of the return channel 72, but the first liquid 82 is prevented from entering the tunnel 64 because of the position of the window 70 above the liquid level $L_1$.

The air in the bubbles emerges from the diffusion chamber 78 through the holes in the diffuser panel 80, then breaks the surface of the liquid level $L_1$, which may cause splashing of the liquid 82 in the first module 14. To reduce the impact of such splashing, a trap 88 is positioned above the diffuser panel 80. The trap 68 can be a separate unit or, as shown in the drawings, formed of the walls of the housing 24, the panel 74, the connecting wall 86, and a barrier wall 90 extending across the top of chamber 88 and the trap 88 as shown in FIGS. 2, 3 and 4, and also in spanning relationship covering the dead-air space 34 between the inner wall 30 and outer wall 32. Thus configured, portion of the connecting wall 86 forming a part of the trap 88 extends downwardly from the barrier wall 90 to edge 92 so that liquid caught in the trap 88 can drain down to return to the first liquid 82 within the first module main chamber 84. The air then moves from the first module main chamber 84 by passing upwardly and through an entranceway 94 in the connecting wall 86 positioned above the barrier wall 90 to enter a tubular extension 96. The tubular extension 96 projects upwardly and into a receiver 98 of the second module 16. The housing 24 includes a top wall 99 which substantially encloses the first module main chamber 84 and the chamber 84 may receive first liquid 82 through a first inlet 100 and is provided with a first discharge outlet 102 for draining the first liquid 82 from the first module 14. Both the first inlet 100 and the first discharge outlet 102 may be provided with suitable caps, fittings, stopcocks or valves as is known by those or ordinary skill in the art.

Figure 5:
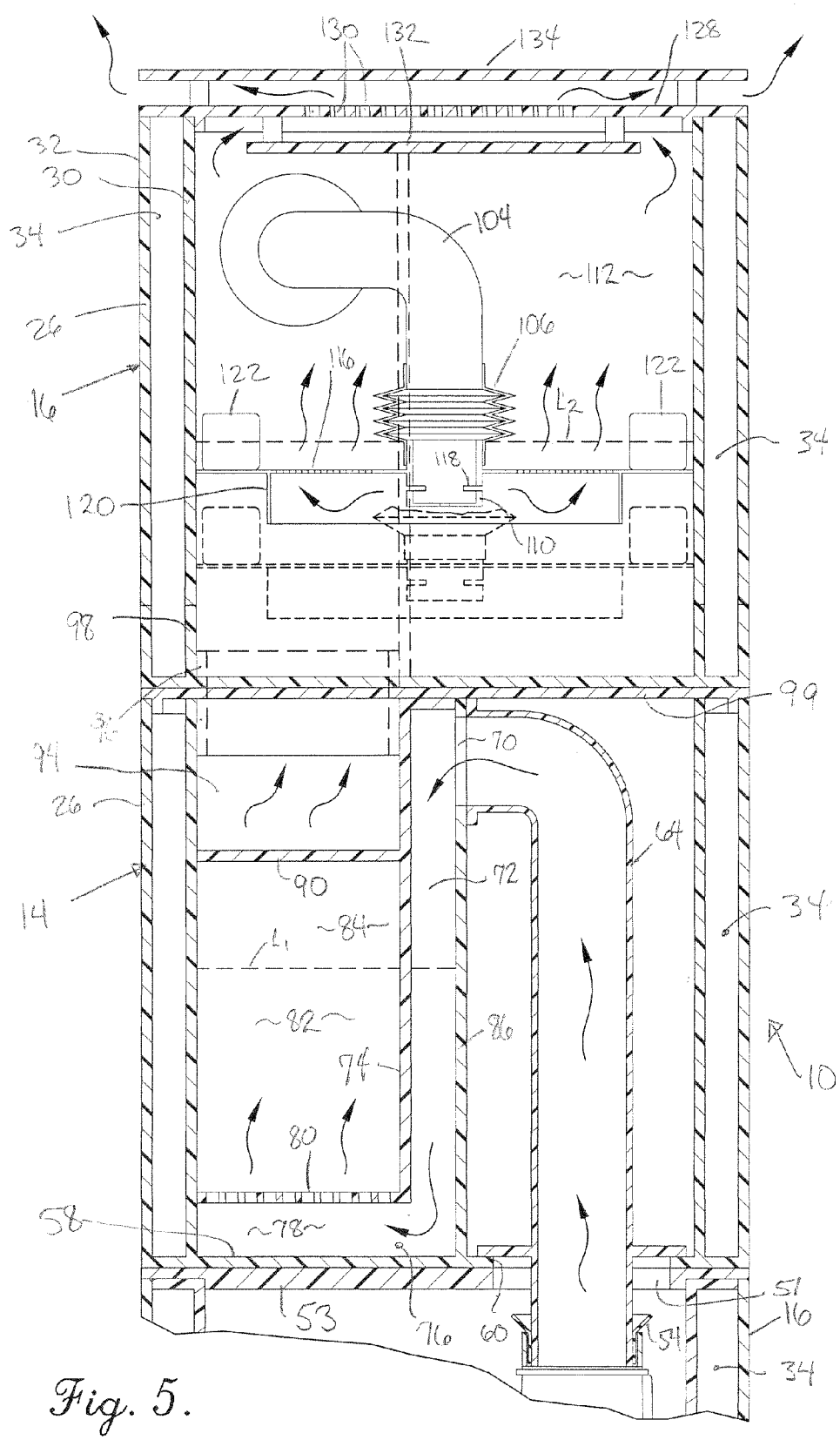
FIG. 5 is an enlarged vertical cross-sectional view of the second module and the upper portion of the first module taken from the rear of the device and showing in broken lines the liquid levels in the respective chambers of the first and second modules, and the alternate positions of the floating sparger in the second module depending on liquid level.

The air passes from the tubular extension 96 upwardly into the second module 16. The housing 26 of the second module 16 like fan module 12 and first module 14 has a surrounding side wall including inner wall 30 and outer wall 32 which substanially encloses a primary chamber 112. As best seen in FIGS. 2, 3 and 4, the tubular extension 96 interfits with and is telescopically received by receiver 98 of the second module 16, the tubular extension 96 conveying the air upwardly to pipe 104, to which flexible tubing 106 is fluidically connected. A distributor 108 is connected to the flexible tubing 106 by force fitting or by a coupler 110 for distributing the flow of air received from the flexible tubing 106. The flexible tubing is very flexible to enable the distributor 108 to freely move up and down according to the amount of liquid in the second module 16, and may be, for example, of very thin walled synthetic resin such as polyethylene, or corrugated as shown in the drawings, but in either instance does not resist the up and down movement of the distributor according to the liquid level $L_2$ as shown in broken lines in FIG. 5. The distributor 108 is positioned within primary chamber 112 of the second module 16 which includes a quantity of a second liquid 114 having a liquid level $L_2$. Because the level $L_2$ may change during use, the distributor 108 is operatively connected to the flexible tubing to permit at least up and down movement of the distributor 108 according to the quantity of liquid within the primary chamber 112 and configured and arranged so that a perforated upper wall 116 of the distributor 108 provided with a plurality of holes is below the liquid level $L_2$. This configuration permits the flow of air moving from the flexible tubing 106 and into the distributor 108 to be broken up into small bubbles and increase the contact between the air and the second liquid 114 so that the distributor 108 acts as a sparger. The coupler 110 may include opposed partially circumferentially extending slots 118 through which air passes to distributor 108. A perimeter wall 120 extends downwardly from perforated upper wall 116 to retain the air received from the flexible tubing 106 therein prior to passage of the upwardly through the holes of the perforated upper wall 116. Floats 122 may be mounted on the upper wall 116 or the perimeter wall 120 to ensure that the distributor 108 remains above the bottom wall 124 of the housing 26 and adjusts to the liquid level $L_2$. To maintain the alignment of the distributor 108 within the primary chamber 112 of the second module 16, the distributor 108 may substantially span the distance between opposing inner panels 30 of opposing sidewalls 28, or other structural members such as upright tracks may provided along opposite sidewalls of the housing 26, with the distributor 108 being provided with complementally configured guides extending to engage the tracks. The flexible tubing 106 is sufficiently flexible to enable the distributor 108 to rise and fall with the second liquid level as shown in FIG. 5. The second module primary chamber 112 may receive second liquid 114 through a second inlet 124 and is provided with a second discharge outlet 126 for draining the second liquid 114 from the second module 16. Both the second inlet 124 and the second discharge outlet 126 may be provided with suitable caps, fittings, stopcocks or valves as is known by those or ordinary skill in the art.

The second module 16 has a top wall 128 which is provided with slots 130 or other openings to permit the air conditioned within the apparatus 10 to pass into the ambient atmosphere. A baffle 132 is spaced downwardly from the top wall 128 and positioned between the slots 130 in the top wall 128 and the liquid level $L_2$ in order to extend the air flowpath, impede the transmission of sound, and inhibit splashing or liquid other than vapor within the air from escaping through the slots 130 in the top wall 128 and to return such liquid received thereon back into the second liquid 114 within the primary chamber 112 of the second module 16. A deflector 134 is mounted in spaced relationship above the top wall 128 for evenly distributing the air passing through the slots 120 and to permit objects to be placed atop the apparatus 10.

As previously mentioned, the apparatus 10 preferably operates to capture and/or disinfect contaminants in the air passing therethrough, in addition to humidifying and purifying the air. In the general method, the initial stream of air to be treated is contacted with a first liquid to yield a first treated air stream. The first treated air stream is then contacted with a second liquid different from the first liquid to yield a second treated air stream, such that the second treated air stream comprises substantially less contaminants than the initial stream of air to be treated. More preferably, the first treated stream has less contaminants than the initial stream, and even more preferably, the second treated stream has less contaminants than the first treated stream. Thus, in the preferred method, the air flow exiting the apparatus 10 preferably comprises substantially less contaminants than the air flow entering the apparatus 10. Air contaminants or pollutants that can be captured include those selected from the group consisting of particulate matter, gaseous pollutants, and combinations thereof. Examples of particulate matter include those selected from the group consisting of dust, dust mites, pollen, animal dander, tobacco smoke, smoke from cooking, mold spores, bacteria, viruses, and particles associated with such organisms. Gaseous pollutants include combustion gases from gas cooking stoves (e.g., carbon monoxide, $CO_2$, nitrogen compounds, such as nitrogen oxide), ozone, and volatile organic compounds (VOCs) from off-gassing of building materials (e.g., adhesives, paints, varnishes, etc.), cleaning products, and pesticides. In the method, the first liquid preferably traps at least a portion of the particulates and/or reacts with and captures at least a portion of the gaseous pollutants in the air.

Preferably, the second liquid also disinfects at least a portion of the particulate matter. More particularly, these contaminants are preferably captured in the first and/or second liquids 82, 114 that are preferably contained in the apparatus 10.

In more detail, the first liquid 82 (in the first module 14) is preferably an aqueous alkaline solution (i.e., having a pH greater than about 7, more preferably greater than about 8.5, and even more preferably from about 10 to about 13). Suitable bases for use in the aqueous solution in the first module 14 are selected from the group consisting of alkalis, alkaline earth metals, and the hydroxides, silicates, phosphates, and carbonates thereof. Preferred alkalis are selected from the group consisting of sodium and potassium. Preferred alkaline earth metal are selected from the group consisting of calcium and magnesium. The base is preferably included in the solution at a concentration of from about 0.1% to about 1.0% by weight, and more preferably at a concentration of from about 0.3% to about 0.8% by weight, based upon the volume of the total solution taken as 100% by volume. Particularly preferred first liquids 82 include aqueous solutions of a base selected from the group consisting of sodium hydroxide, potassium hydroxide, sodium metasilicate, sodium carbonate, calcium carbonate, magnesium phosphate, sodium bicarbonate, trisodium phosphate, and mixtures thereof. Suitable first liquids 82 can be formed, for example, by dispersing the base in water (tap, bottled, distilled, etc.). The base compound can be separately added, or it can be added as part of a stock alkaline solution. In particular, when aqueous sodium hydroxide is utilized as the alkaline solution, the first liquid 82 can be formed by mixing up to about 1 oz. of a NaOH (98%) solution with about 1 gallon of water, with the resulting solution comprising about 0.76% base. Depending upon the second liquid 114 used, as discussed in more detail below, the concentration of the first liquid 82 can be decreased to about 0.5 oz. of NaOH (98%) solution in 1 gallon of water, with the resulting solution comprising about 0.38% base. For example, if the second liquid 114 comprises only water, the amount of base utilized in the first liquid 82 can be decreased. It will be appreciated that the specific amounts of the stock solution utilized to achieve the indicated concentrations will depend upon the initial concentration of the stock solution, and can be calculated without undue experimentation. However, in a preferred embodiment, the first liquid 82 preferably comprises from about 0.5 oz. to about 1.0 oz. of NaOH (98%) in about 1 gallon of water.

As mentioned, the first liquid 82 preferably captures contaminants from the air passing through the liquid by trapping particulates in the air and also reacting with, and capturing, gasses in the air. For example, in a preferred embodiment, the water in the first liquid 82 reacts with $CO_2$ in the air to produce carbonic acid ($H_2CO_3$), which in turn reacts with the base to produce a salt (i.e., carbonate) according to Reaction Scheme A below (using aqueous NaOH).

Reaction Scheme A

  (1)

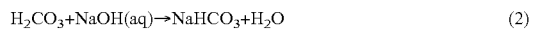  (2)

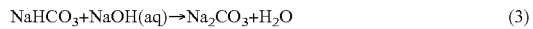  (3)

As the air passes from the first module 14, it is preferably passed through the second liquid 114 (which is contained in the primary chamber 112 of the second module 16). The second liquid 114 preferably dilutes, removes, and/or neutralizes any residual base (or salt thereof) in the air carried from the first module 14. Preferably, the second liquid 114 also further treats and/or disinfects the air passing therethrough. Those of ordinary skill in the art will appreciate that a variety of suitable liquids for use in the second module 16 can be selected, depending upon the aqueous alkaline solution utilized as the first liquid 82 in the first module 14. Preferably, the second liquid 114 comprises water and may include a disinfecting and/or neutralizing agent. More preferably, the second liquid 114 will comprise an aqueous dispersion or solution comprising a compound or source of a compound selected from the group consisting of a chlorines, bromines, quaternary ammonium compounds, organic acids, and non-hazardous mixtures thereof. The term "non-hazardous mixture" refers to mixtures that do not result in a volatile (i.e., explosive), toxic, or otherwise hazardous reaction product. The compound is preferably present in the solution or dispersion at a concentration of from about 0.001% to about 0.005% by weight, and more preferably from about 0.002% to about 0.003% by weight, based upon the total volume of the solution taken as 100% by weight. Suitable chlorines for use in the aqueous solution of the second liquid 114 are selected from the group consisting of sodium hypochlorite, lithium hypochlorite, calcium hypochlorite, chloroisocyanuric acid (di- and tri-), sodium chloro-s-triazinetrione (di- and tri-), sodium di chloro-s-triazinetrione dihydrate, and combinations thereof. Suitable bromines are selected from the group consisting of bromochloro-5,5-dimethylhydantoin, and combinations thereof. Exemplary quaternary ammonium compounds are selected from the group consisting of benzalkonium chloride, benzethonium chloride, methylbenzethonium chloride, cetalkonium chloride, cetylpyridinium chloride, cetrimonium (chloride, bromide, or stearate), cetrimide, dofanium chloride, tetraethylammonium bromide, didecyldimethylammonium chloride, domiphen bromide, and mixtures thereof. Preferred organic acids are selected from the group consisting of acetic acid, citric acid, and mixtures thereof. A particularly preferred disinfecting agent will comprise a source of hypochlorous acid (i.e., a compound that dissolves or dissociates in water to release hypochlorous acid and ultimately chlorine), such as sodium hypochlorite or bromochloro-5,5-dimethylhydantoin. In such embodiments, the second liquid 114 preferably comprises less than about 100 ppm free (available) chlorine, and more preferably from about 50 to about 100 ppm free chlorine. Suitable second liquids 114 can be formed, for example, by dispersing the disinfecting agent in water (tap, bottled, distilled, etc.). The disinfecting agent compound can be separately added or it can be mixed with the water as part of a stock solution. For example, a diluted solution of sodium hypochlorite (bleach) can be used to prepare the second liquid 114. In particular, from about 1/32 oz. to about 1/8 oz. (and preferably about 1/16 oz.) of common household bleach (~5.25 wt % sodium hypochlorite) can be dispersed in about 1 gallon of water to form a suitable aqueous disinfecting agent for the second liquid 114.

The air passing from the first module 14 into the primary chamber 112 of the second module 16 will preferably be further treated (i.e., disinfected) by the second liquid 114, which also serves to neutralize any residual base in the air from the first module 14. For example, when aqueous sodium hypochlorite is the second liquid 114, it will dissociate into hypochlorous acid and hydrochloric acid (among other things) in solution. When aqueous sodium hydroxide is the first liquid 82 (see Reaction Scheme A above), the hypochlorous acid and hydrochloric acid in the second liquid 114 will react with, and preferably neutralize, any residual NaOH or sodium carbonate ($Na_2CO_3$) passing into the second module 16, to minimize the compounds in the purified air passing through into the ambient atmosphere.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of his invention as pertains to any apparatus not materially departing from but outside the literal scope of the invention as set out in the following claims.

The invention claimed is:

1. A device for conditioning air within an enclosed space comprising:
    a fan for generating a flow of air;
    a first module for receiving the flow of air from the fan, said first module including a first housing and having a first chamber located within the housing adapted for holding a quantity of a first liquid, a diffuser located within the chamber, and a channel for conveying the flow of air to the diffuser and arranged to prevent first liquid within the first chamber from flowing into the fan; and
    a second module including a flexible tube in fluidic communication with the first module for receiving a flow of air from the first module, said second module including a second housing, a primary chamber within the housing adapted for holding a second liquid, and a distributor arranged for dispersing and delivering the flow of air into the second liquid, said distributor being positioned within the primary chamber and operatively connected to the flexible tubing whereby said distributor may move upwardly and downwardly according to the amount of second liquid within the primary chamber.

2. A device for conditioning air as set forth in claim 1, wherein said second module is positioned atop said first module.

3. A device for conditioning air as set forth in claim 2, wherein said diffuser is fixed within the housing.

4. A device for conditioning air as set forth in claim 3, wherein the first module includes a trap positioned above the diffuser arranged for limiting the flow of first liquid into the second module.

5. A device for conditioning air as set forth in claim 2, wherein the first module is removably mounted to the second module and includes an extension which interfits with a receiver in the second module for conveying the flow of air from the first module to the second module.

6. A device for conditioning air as set forth in claim 5, wherein the receiver is configured to prevent second liquid in the primary chamber of the second module from flowing downwardly into the first chamber of the first module.

7. A device for conditioning air as set forth in claim 2, wherein the first module is positioned atop the fan module.

8. A device for conditioning air as set forth in claim 1, wherein the fan module includes filter media for filtering particles from the flow of air prior to said flow entering the first module.

9. A device for conditioning air as set forth in claim 1, including a first liquid within the first chamber, wherein said first liquid is an aqueous alkaline solution.

10. A device for conditioning air as set forth in claim 9, wherein said aqueous alkaline solution comprises a base selected from the group consisting of alkalis, alkaline earth metals, and the hydroxides, silicates, phosphates, and carbonates thereof.

11. A device for conditioning air as set forth in claim 1, including a second liquid in the primary chamber, wherein said second liquid comprises water.

12. A device for conditioning air as set forth in claim 11, said second liquid further comprising a disinfecting or neutralizing agent selected from the group consisting of chlorines, bromines, quaternary ammonium compounds, organic acids, and non-hazardous mixtures thereof.

13. A method for conditioning air within an enclosed space comprising the steps of:
    providing a device including a fan, a first module including a first chamber and a diffuser positioned in the first chamber, and a second module including a primary chamber having a distributor positioned in the primary chamber and fluidically connected to said first module;
    providing a sufficient quantity of a first liquid in said first chamber in order to position at least a part of the diffuser positioned below a liquid level of the first liquid, wherein said first liquid is an aqueous alkaline solution;
    providing a sufficient quantity of a second liquid in said primary chamber in order that at least a part of the distributor beneath a liquid level of the second liquid;
    generating a flow of air directed from said fan into said first module;
    causing said flow of air to pass through said diffuser such that the flow of air is broken into bubbles within the first liquid;
    causing air to flow from the first module and be delivered to the distributor;
    causing air to flow through the distributor such that the flow of air is broken into bubbles within the second liquid; and
    delivering the air to the environment after passage of the air through the distributor.

14. A method for conditioning air as set forth in claim 13, wherein said aqueous alkaline solution comprises a base selected from the group consisting of alkalis, alkaline earth metals, and the hydroxides, silicates, phosphates, and carbonates thereof.

15. A method for conditioning air as set forth in claim 13, wherein said second liquid comprises water.

16. A method for conditioning air as set forth in claim 15, said second liquid further comprising a disinfecting or neutralizing agent selected from the group consisting of chlorines, bromines, quaternary ammonium compounds, organic acids, and non-hazardous mixtures thereof.

17. A method for conditioning air as set forth in claim 13, wherein said air comprises contaminants, said step of causing said flow of air to pass through said diffuser comprises capturing contaminants from said air in said first liquid.

18. A method for conditioning air as set forth in claim 17, said step of causing air to flow through the distributor comprising disinfecting said contaminants in said air.

19. A device for conditioning air within an enclosed space comprising:
    a fan for generating a flow of air;
    a first module for receiving the flow of air from the fan, said first module including a first housing and having a first chamber located within the housing holding a quantity of a first liquid, a diffuser located within the chamber, and a channel for conveying the flow of air to the diffuser and arranged to prevent the first liquid within the first chamber from flowing into the fan, wherein said first liquid comprises an aqueous solution of a base selected from the group consisting of sodium hydroxide, potassium hydroxide, sodium metasilicate, sodium carbonate, calcium carbonate, sodium bicarbonate, trisodium phosphate, and mixtures thereof; and a second module including a flexible tube in fluidic communication with the first module for receiving a flow of air from the first module, said second module including a second housing, a primary chamber within the housing for holding a second liquid, and a distributor for dispersing and delivering the flow of air into the second liquid, said distributor being positioned within the primary chamber and operatively connected to the flexible tubing whereby said distributor may move upwardly and downwardly according to the amount of liquid within the primary chamber.

20. A device for conditioning air as set forth in claim 19, wherein said second liquid comprises water and a disinfecting or neutralizing agent selected from the group consisting of chlorines, bromines, quaternary ammonium compounds, organic acids, and non-hazardous mixtures thereof.

21. A method for treating a stream of air containing contaminants comprising:
    contacting an initial stream of air to be treated with a first liquid comprising an aqueous alkaline solution to yield a first treated air stream;
    contacting said first treated air stream with a second liquid different from said first liquid and comprising water to yield a second treated air stream, said second treated air stream comprising substantially less contaminants than said initial stream of air to be treated.

22. The method of claim 21, wherein said first liquid comprises an aqueous solution of a base selected from the group consisting of sodium hydroxide, potassium hydroxide, sodium metasilicate, sodium carbonate, calcium carbonate, sodium bicarbonate, trisodium phosphate, and mixtures thereof.

23. The method of claim 21, wherein said second liquid comprises water and a disinfecting or neutralizing agent selected from the group consisting of chlorines, bromines, quaternary ammonium compounds, organic acids, and non-hazardous mixtures thereof.

24. The method of claim 21, wherein said contaminants are selected from the group consisting of particulate matter, gaseous pollutants, and combinations thereof.

25. The method of claim 24, said first liquid trapping at least a portion of said particulate matter.

26. The method of claim 24, said first liquid reacting with and capturing at least a portion of said gaseous pollutants.

27. The method of claim 24, said second liquid disinfecting at least a portion of said particulate matter.

28. The method of claim 21, wherein said first treated stream has less contaminants than said initial stream.

29. The method of claim 21, wherein said second treated stream has less contaminants than said first treated stream.

30. A device for conditioning air within an enclosed space comprising:
    a fan for generating a flow of air; and
    a module including a housing chamber receiving said fan therein, said housing having a top wall, a bottom wall and a side wall substantially surrounding said chamber, and including an inlet through said housing for the introduction of air into said chamber and an opening in said housing for discharging air from said housing,
    wherein said surrounding side wall of said housing includes an inner wall and an outer wall defining a space therebetween, and
    wherein said inlet into said housing includes at least one sound suppression panel placed in alignment with said opening.

31. A device as set forth in claim 30, wherein said module is a fan module and further including:
    a filtering media in said module for filtering air entering said inlet prior to discharge through said opening;
    a first module for receiving the flow of air from the fan, said first module including a first housing and having a first chamber located within the housing adapted for holding a quantity of a first liquid.

32. A device as set forth in claim 31, including a second module in fluidic communication with the first module for receiving a flow of air from the first module, said second module including a second housing, a primary chamber within the housing adapted for holding a second liquid.

33. A device as set forth in claim 32, wherein the first housing and the second housing each have substantially surrounding side walls including spaced apart inner wall and outer walls providing a space therebetween.

34. A device as set forth in claim 30, wherein said bottom wall of said housing includes a lowermost outer bottom wall and an inner bottom wall spaced thereabove defining a space therebetween.

35. A device as set forth in claim 30, wherein said at least one sound suppression panel is an inner sound suppression panel located within said housing interiorly of said opening and sized greater than said opening, and further including an outer sound suppression panel located exteriorly of said opening in alignment with said opening and sized greater than said opening.

* * * * *